(12) United States Patent
Shen et al.

(10) Patent No.: US 9,347,925 B2
(45) Date of Patent: May 24, 2016

(54) METHOD OF CALIBRATING AN AIR SENSOR

(75) Inventors: Fangzhong Shen, Shanghai (CN); Hong Zhang, Beijing (CN); Gerd Lanfermann, Aachen (DE)

(73) Assignee: KONINKLIJKE PHILIPS N.V., Eindhoven (NL)

( * ) Notice: Subject to any disclaimer, the term of this patent is extended or adjusted under 35 U.S.C. 154(b) by 268 days.

(21) Appl. No.: 13/881,957

(22) PCT Filed: Oct. 28, 2011

(86) PCT No.: PCT/EP2011/068984
§ 371 (c)(1),
(2), (4) Date: Jun. 7, 2013

(87) PCT Pub. No.: WO2012/059425
PCT Pub. Date: May 10, 2012

(65) Prior Publication Data
US 2013/0247643 A1    Sep. 26, 2013

(30) Foreign Application Priority Data
Nov. 1, 2010 (WO) ................. PCT/CN2010/078280

(51) Int. Cl.
*G01N 33/00* (2006.01)
*B01D 53/30* (2006.01)
(Continued)

(52) U.S. Cl.
CPC ............ *G01N 33/0006* (2013.01); *B01D 53/30* (2013.01); *B60H 1/008* (2013.01); *B01D 2258/06* (2013.01); *B01D 2259/4566* (2013.01); *F24F 3/1603* (2013.01)

(58) Field of Classification Search
CPC ................. G01N 33/0006; G01N 35/00594; G01N 35/00693; B60H 3/0608
See application file for complete search history.

(56) References Cited

U.S. PATENT DOCUMENTS

| 4,384,925 A | 5/1983 | Stetter et al. |
| 4,499,377 A | 2/1985 | Presser |

(Continued)

FOREIGN PATENT DOCUMENTS

| CN | 201540242 U | 8/2010 |
| DE | 29723567 U1 | 4/1999 |

(Continued)

OTHER PUBLICATIONS

Wataru Tsujita et al, "Gas sensor network for air-pollution monitoring", Sensors and Actuators, B 110 (2005) pp. 304-311, www.sciencedirect.com.

(Continued)

*Primary Examiner* — David A Rogers

(57) ABSTRACT

One embodiment of the invention provides an air treatment device. The air treatment device comprises: an air purifying unit, configured to purify air; an air sensor, configured to measure a first air quantity and provide a measurement output, wherein the first air quantity comprises the purified air purified by the air purifying unit; and a processor, configured to generate a first value based on the measurement output of the air sensor so as to calibrate the air sensor. With the air treatment device of one embodiment of the invention, clean air, i.e. zero air, is generated locally by the air treatment device so as to calibrate the air sensor, without the need for externally generating the zero air, which brings convenience for the user or other operators performing calibration of the air sensor of the air treatment device. Another embodiment of the invention also provides a method of calibrating an air sensor of an air treatment device. The method comprises the steps of: purifying air by using the air treatment device; and measuring a first air quantity by using the air sensor to get a first value so as to calibrate the air sensor, wherein the first air quantity comprises the purified air.

12 Claims, 1 Drawing Sheet

(51) Int. Cl.
*B60H 1/00* (2006.01)
*F24F 3/16* (2006.01)

(56) References Cited

U.S. PATENT DOCUMENTS

| | | | |
|---|---|---|---|
| 4,658,707 A * | 4/1987 | Hawkins et al. ............... 454/75 |
| 4,827,154 A | 5/1989 | Naoyuki |
| 5,046,018 A * | 9/1991 | Flewelling et al. ............ 702/24 |
| 5,221,292 A * | 6/1993 | Aoyama ........................ 96/142 |
| 5,239,492 A * | 8/1993 | Hartwig et al. ............... 702/27 |
| 5,325,705 A * | 7/1994 | Tom ............................. 73/31.03 |
| 5,792,427 A * | 8/1998 | Hugh et al. .................... 422/109 |
| 6,632,674 B1 | 10/2003 | Warburton |
| 8,452,489 B2 | 5/2013 | Marra |
| 2003/0143129 A1* | 7/2003 | Rabellino et al. ............. 422/171 |
| 2003/0154031 A1* | 8/2003 | Potyrailo et al. .............. 702/19 |
| 2005/0252273 A1 | 11/2005 | Imoto |
| 2006/0026936 A1* | 2/2006 | Paumier et al. ................ 55/473 |
| 2007/0012181 A1 | 1/2007 | Niezgoda et al. |
| 2007/0078608 A1* | 4/2007 | Broy ............................. 702/24 |
| 2008/0053439 A1* | 3/2008 | Lighton .................. 128/204.22 |
| 2009/0113984 A1* | 5/2009 | Gautieri et al. ............... 73/1.07 |
| 2010/0282958 A1* | 11/2010 | Will et al. ................. 250/252.1 |
| 2011/0046497 A1* | 2/2011 | Abraham-Fuchs et al. .. 600/532 |
| 2011/0208081 A1* | 8/2011 | Smith et al. .................. 600/532 |

FOREIGN PATENT DOCUMENTS

| | | |
|---|---|---|
| EP | 1402935 A1 | 3/2004 |
| FR | 2708995 A1 * | 2/1995 |
| JP | 5096943 A | 4/1993 |
| JP | 06272919 A | 9/1994 |
| JP | 11166912 A | 6/1999 |
| JP | 2003172695 A | 6/2003 |
| JP | 2006064494 A | 3/2006 |
| JP | 2006177863 A | 7/2006 |

OTHER PUBLICATIONS

M.A. Ryan et al, "Monitoring Space Shuttle Air for Selected Contaminants Using an Electronic Nose", http://trs-new.jpl.nasa.gov/dspace/bitstream/2014/19480/1/98-0888.pdf, 1998.

http://www.permapure.com/wp/wp-content/uploads/calibration.pdf?ind=customer-applications Created on Mar. 24, 2010.

* cited by examiner

METHOD OF CALIBRATING AN AIR SENSOR

FIELD OF THE INVENTION

The invention relates to the field of air treatment, in particular a method of calibrating an air sensor of an air treatment device.

BACKGROUND OF THE INVENTION

Urbanization and industrialization cause air pollution in megacities, especially in emerging markets. For purifying the air to improve air quality, air treatment devices are widely used in homes, offices and automobiles.

An air quality indicator is usually integrated in the air treatment device to give the user an indication of the air quality. In this manner, the air treatment device may further comprise an air sensor and a processor. The air sensor measures the air quality and provides a measurement output, and then the processor reads the measurement output of the air sensor and controls the air quality indicator to give an indication to the user based on the measurement output of the air sensor. However, the measurement output of the air sensor may drift over time, and the air sensor itself may also show inconsistencies between measurements, even in the same batch, as a result of which the air quality indicator may give a wrong indication to the user; consequently, it is hard for the user to check whether the indoor air quality has really improved, which is annoying and may reduce people's confidence in the air treatment device.

SUMMARY OF THE INVENTION

Normally, zero air is to be used to calibrate the air sensor. However, each time the air sensor of the air treatment device is required to be calibrated, the user has to make efforts to find zero air to perform the calibration, which is quite inconvenient.

In view of the above issues, it would be advantageous to achieve a method of calibrating an air sensor of an air treatment device, wherein the clean air, i.e. zero air, for calibrating the air sensor is generated locally by the air treatment device. And it would also be desirable to achieve an air treatment device of which the air sensor can be calibrated with the clean air, i.e. zero air, generated locally by the air treatment device.

To better address the above concern, according to one embodiment of the invention, there is provided an air treatment device comprising:
  an air purifying unit configured to purify air;
  an air sensor configured to measure a first air quantity and provide a measurement output, wherein the first air quantity comprises the purified air purified by the air purifying unit; and
  a processor configured to generate a first value based on the measurement output of the air sensor so as to calibrate the air sensor.

In an embodiment, the first air quantity is the purified air, and then the air treatment device further comprises:
  a switch arranged between the air sensor and the air purifying unit;
  wherein the processor is further configured to open or close the switch to allow the purified air flow to the air sensor or block the purified air flow to the air sensor.

In another embodiment, the first air quantity is the mixture of ambient air and the purified air, and the air treatment device is placed in an airtight space, and the processor is further configured to determine whether the quality of the first air quantity in the airtight space meets a predefined criterion, and to generate the first value based on the measurement output of the air sensor if the quality of the first air quantity meets the predefined criterion.

With the air treatment device of one embodiment of the invention, the clean air, i.e. zero air, is generated locally by the air treatment device so as to calibrate the air sensor, without the need for externally generating the zero air, which brings convenience for the user or other operators performing calibration of the air sensor of the air treatment device. Furthermore, as the measurement output of the air sensor is calibrated, the indication of the air quality provided to the user will be accurate.

According to another embodiment of the invention, there is provided a method of calibrating an air sensor of an air treatment device, the method comprising the steps of:
  purifying air by using the air treatment device; and
  measuring a first air quantity by using the air sensor to get a first value so as to calibrate the air sensor, wherein the first air quantity comprises the purified air.

These and other aspects of the invention will be apparent from and elucidated with reference to the embodiments described hereinafter.

DESCRIPTION OF THE DRAWINGS

The above and other objects and features of the present invention will become more apparent from the following detailed description considered in connection with the accompanying drawings, in which.

The same reference numerals are used to denote similar parts throughout the figures.

DETAILED DESCRIPTION

Figure 1:
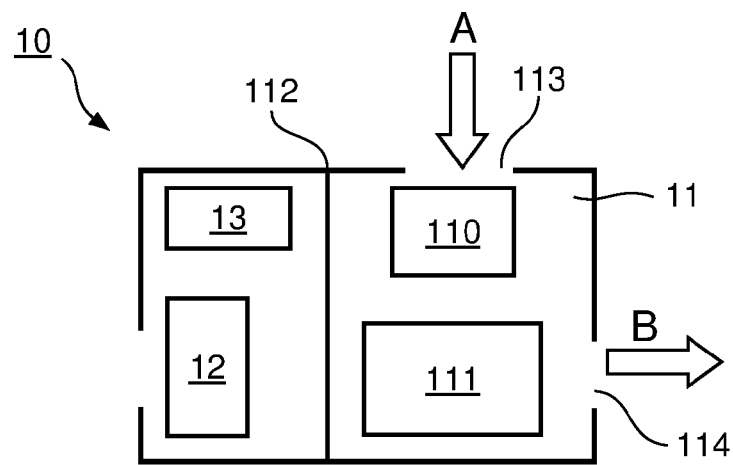
FIG. 1 depicts an exemplary air treatment device 10 according to one embodiment of the invention.

FIG. 1 depicts an exemplary air treatment device 10 according to one embodiment of the invention. The air treatment device 10 may generally be used in homes, offices, automobiles, and other (public) places, to purify the air. As shown in FIG. 1, the air treatment device 10 comprises an air purifying unit 11, an air sensor 12, and a processor 13.

The air purifying unit 11 may take on any configuration, but generally includes a filtering means 110 and a motor 111 as shown in FIG. 1. The filtering means 110 may generally include a particle filtering unit for filtering particles, such as dust, from passing air for example, and a gas filtering unit for filtering gases, such as chemical gases, from passing air for example. The motor 111 is configured to cause the air to be purified to pass through the filtering means 110, which may be a backward impeller for example. The air purifying unit 11 may further include a housing 112 having an inlet area 113 and an outlet area 114, respectively, configured to allow the air to be purified to enter (denoted by arrow A) and exit (denoted by arrow B) the air purifying unit 11. The filtering means 110 and the motor 111 may both be enclosed in the housing 112, as shown in FIG. 1.

The air sensor 12 may be any form of sensor which is suitable for measuring the air quality, such as a particle sensor or a gas sensor for example. The air sensor 12 is configured to measure the air quality and provide the measurement output to the processor 13, which may be a Micro Control Unit (MCU) for example.

In the normal working mode, once the air treatment device 10 in for example an automobile is activated, the motor 111 starts to suck ambient air present in the cabin of the automobile into the air purifying unit 11 via the inlet area 113. The ambient air then passes through the filtering means 110 which filters for example dust and chemical gases from the passing ambient air, and then the purified air exits the air purifying unit 11 via the outlet area 114 and mixes with the ambient air in the cabin. The above described process is repeated during the normal working mode of the air treatment device 10 so as to purify the air in the cabin.

The air sensor 12 measures the quality of the air in the cabin and provides a measurement output. The processor 13 reads the measurement output of the air sensor 12 and then gives the air quality indication to the user, based on the measurement output of the air sensor 12. A quality indicator, for example one LED or an array of LEDs, may be arranged on the air treatment device 10 to give an indication of the air quality. When the processor 13 reads the measurement output of the air sensor 12, it may compare the measurement output of the air sensor 12 with a predefined threshold, and then control the LED to turn green, which indicates that the air quality is pleasant if the measurement output of the air sensor 12, for example, does not exceed the predefined threshold, or control the LED to turn red, which indicates that the air quality is poor if the measurement output of the air sensor 12, for example, exceeds the predefined threshold. It will be appreciated that more than one threshold may be defined to determine the air quality, and in this regard the LED may be controlled to take on more than two colors to give an indication of different air quality levels.

When the air sensor 12 of the air treatment device 10 is required to be calibrated, for example because the measurement output of the air sensor 12 drifts over time, causing the indication of the air quality by the indicator to be inaccurate, the air treatment device 10 goes into the calibration mode.

In one embodiment, the air treatment device 10 may comprise a user interface, and the calibration mode may be activated when an instruction through the user interface is received, for example when a calibration key on the air treatment device 10 is pressed. Alternatively, the calibration mode may be automatically activated, for example periodically, without the need for an instruction from the user or other operators.

Advantageously, the calibration mode may be activated after the filtering means 110 of the air purifying unit 11 has been washed or replaced.

When the calibration mode is activated, the air purifying unit 11 of the air treatment device 10 starts to purify the air in the cabin. As described above, in the normal working mode, the ambient air in the cabin is sucked into the air purifying unit 11 via the inlet area 113 by the motor 111 and passes through the filtering means 110, and then the purified air exits the air purifying unit 11 via the outlet area 114 and mixes with the ambient air in the cabin. The operation of the air purifying unit 11 is repeated so as to purify the air in the cabin.

The air sensor 12 measures said mixture of purified air and ambient air, and provides a measurement output. The processor 13 determines whether the quality of the mixture meets a predefined criterion, based on the measurement output of the air sensor 12, and generates a first value based on the measurement output of the air sensor 12 if the quality of the mixture meets the predefined criterion, so as to calibrate the air sensor 12. It is to be noted that the air in the cabin can substantially be referred to as zero air if the quality of the mixture meets the predefined criterion, and consequently the first value can be regarded as the measurement output of the air sensor 12 at zero air.

In one embodiment, the moving average algorithms may be used to determine whether the quality of the mixture meets a predefined criterion. For illustrative purposes only, the operation of the processor 13 will be described by taking the window size to be ten and the sampling interval to be one second. To be specific, the processor 13 collects ten measurement outputs of the air sensor 12, i.e. reads the measurement output of the air sensor 12 once every second for ten seconds, and determines whether the standard deviation or variance of the ten measurement outputs is larger than a threshold. If the standard deviation or variance of the ten measurement outputs is larger than the threshold, the processor 13 continues to collect the subsequent ten measurement outputs of the air sensor 12 and performs the operation of determining whether or not the standard deviation or variance of the ten measurement outputs is larger than a threshold; if the standard deviation or variance of the ten measurement outputs is not larger than the threshold, the processor 13 calculates the average of the ten measurement outputs as the first value. Alternatively, the processor 13 may read the current measurement output of the air sensor 12 as the first value if the standard deviation or variance of the ten measurement outputs does not exceed the threshold.

When the first value is achieved, in one embodiment, the processor 13 may further calculate the difference between the first value and a reference value as a compensation value so as to calibrate the measurement output of the air sensor 12. The reference value is the standard output of the air sensor 12 at zero air, which may be pre-stored in the processor 13. The compensation value may be used to compensate the measurement output of the air sensor 12 in the normal working mode, that is, when the air treatment device 10 operates in the normal working mode, the processor 13 will read the measurement output of the air sensor 12 and compensate the measurement output of the air sensor 12 with the compensation value, and thus the indication of the air quality by the quality indicator will be accurate. In this regard, it is desirable that the response of the air sensor 12 is linear.

Alternatively, the processor 13 may change the configuration of the peripheral circuits of the air sensor 12, based on the first value, so as to calibrate the measurement output of the air sensor 12. In this configuration, the direct output of the peripheral circuits surrounding the air sensor can be the direct output of the processor 13, without the need for further compensation.

Advantageously, the progress of the calibration may be indicated by a progress indicator, for example one LED or an array of LEDs on the user interface, emitting light ranging from flashing red colored light, in the progress stage, to static green colored light being an indication of successful completion, which may avoid interruption in-between.

It is to be noted that, in this embodiment, calibration should be performed in an airtight space, for example the airtight cabin of an automobile.

Figure 2:
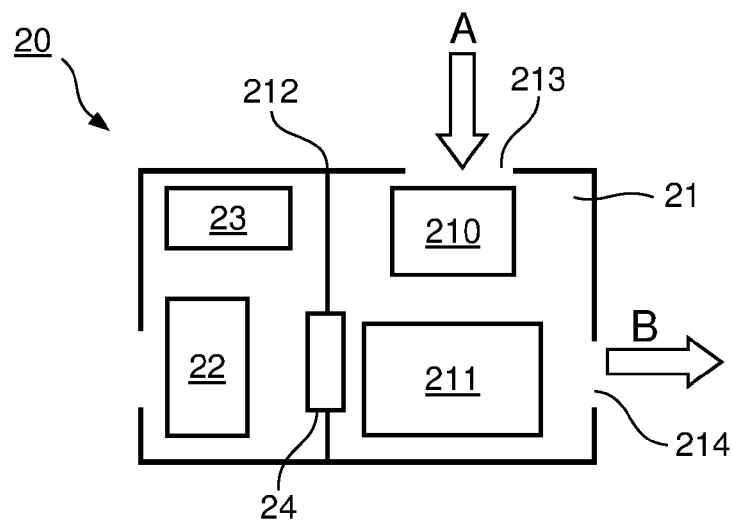
FIG. 2 depicts an exemplary air treatment device 20 according to another embodiment of the invention.

FIG. 2 depicts an exemplary air treatment device 20 according to another embodiment of the present invention. The air treatment device 20 comprises an air purifying unit 21, an air sensor 22, a processor 23 and a switch 24 arranged between the air sensor 22 and the purifying unit 21. The configurations of the air purifying unit 21, the air sensor 22, and the processor 23 are the same as those of the corresponding modules in FIG. 1, and will not be described here for simplicity.

The switch 24 may take on any configuration suitable to be switched on and off, but a flip gate or a sliding cover is preferred.

In one embodiment, the processor 23 is further configured to open or close the switch 24 to allow the air purified by the purifying unit 21 to flow toward the air sensor 22 or to block the purified air flow toward the air sensor 22, respectively. Alternatively, the switch 24 may be switched on or off manually.

In the normal working mode, the switch 24 is closed by the processor 23 so as to block the flow of air purified by the purifying unit 21 toward the air sensor 22, and therefore the operation of each module in the air treatment device 20 to purify the air in the cabin is the same as that described with reference to FIG. 1 and will not be described here for simplicity.

When the air sensor 22 of the air treatment device 20 is required to be calibrated, the air treatment device 10 goes into the calibration mode. The calibration mode may be activated by an instruction from the user or other operators, or may be activated automatically as described with reference to FIG. 1. In the calibration mode, the switch 24 is opened by the processor 23 to allow the air purified by the purifying unit 21 to flow toward the air sensor 22.

When the calibration mode is activated, the air purifying unit 21 of the air treatment device 20 starts to purify the air in the cabin. To be specific, the ambient air in the cabin is sucked into the air purifying unit 21 via the inlet area 213 by the motor 211 and passes through the filtering means 210, and then the purified air exits the air purifying unit 21 via the outlet area 214 and mixes with the ambient air in the cabin. As the switch 24 is open, part of the purified air is also guided toward the air sensor 22. Usually, the air purified by the purifying unit 21 can be considered as zero air; consequently, the current output of the air sensor 22 can be regarded as the output at zero air, i.e. the first value, so as to calibrate the air sensor 22.

It is to be noted that, in this embodiment, as the air purified by the purifying unit 21 is directly provided to the air sensor 22 to get the first value, the calibration can be performed without the need for an airtight space.

Furthermore, as the air purified by the purifying unit 21 is directly provided to the air sensor 22 to get the first value, the air treatment device 20 of FIG. 2 needs less time to finish the calibration than the air treatment device 10 of FIG. 1.

Figure 3:
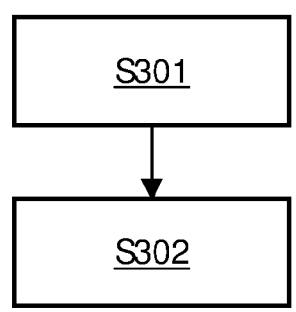
FIG. 3 depicts a flow chart of the method of calibrating an air sensor of an air treatment device according to one embodiment of the invention.

FIG. 3 depicts a flow chart of the method of calibrating an air sensor of an air treatment device according to one embodiment.

First, in step 301, air is purified using the air treatment device.

Then, in step 302, a first air quantity is measured using the air sensor to get a first value so as to calibrate the air sensor, wherein the first air quantity comprises the purified air.

Optionally, after step 302, the method may further comprise a step of: generating a compensation value based on the first value and a reference value so as to calibrate the air sensor, wherein the reference value is a standard output of the air sensor at zero air.

Optionally, the method may further comprise a step of: receiving an instruction through a user interface to start or stop any one of the steps 301 and 302.

In one embodiment, the first air quantity is the purified air, and the subsequent measuring step of step 302 may further comprise the steps of: directing the purified air toward the air sensor; and measuring the purified air by using the air sensor to get the first value.

In another embodiment, the first air quantity is a mixture of ambient air and the purified air, and the air treatment device is placed in an airtight space, and the subsequent measuring step of step 302 may further comprise the steps of: determining whether the quality of the first air quantity in the airtight space meets a predefined criterion; and measuring the first air quantity by using the air sensor to get the first value, if the quality of the first air quantity meets the predefined criterion.

Optionally, the determining step may further comprise the steps of: collecting a plurality of measurement outputs of the air sensor, and determining whether the standard deviation of the plurality of measurement outputs is smaller than a threshold.

According to another embodiment of the present invention, there is provided a set of computer executable instructions configured to perform the steps 301 and 302 of FIG. 3.

It should be noted that the above-mentioned embodiments illustrate rather than limit the invention and that those skilled in the art will be able to design alternative embodiments without departing from the scope of the appended claims. In the claims, any reference signs placed between parentheses shall not be construed as limiting the claim. The word "comprising" does not exclude the presence of elements or steps not listed in a claim or in the description. The word "a" or "an" preceding an element does not exclude the presence of a plurality of such elements. In the apparatus claims enumerating several units, several of these units can be embodied by one and the same item of hardware or software. The use of the words first, second and third, et cetera, does not indicate any ordering. These words are to be interpreted as names.

The invention claimed is:

1. A method of calibrating an air sensor of an air treatment device, the method comprising the steps of:
   i. purifying air by using the air treatment device; and
   ii. measuring a first air quantity by using the air sensor to get a first value so as to calibrate the air sensor, wherein the first air quantity comprises a mixture of ambient air and the purified air, and the air treatment device is placed in an airtight space, and wherein step ii further comprises the steps of:
      determining whether the quality of the first air quantity in the airtight space meets a predefined criterion; and
      if the quality of the first air quantity meets the predefined criterion, measuring the first air quantity by using the air sensor to get the first value.

2. The method as claimed in claim 1, wherein step ii comprises a step of:
   generating a compensation value based on the first value and a reference value so as to calibrate the air sensor, wherein the reference value is a standard output of the air sensor at zero air.

3. The method as claimed in claim 1, wherein step ii further comprises the steps of:
   directing the purified air toward the air sensor.

4. The method as claimed in claim 1, wherein the determining step further comprises the steps of:
   collecting a plurality of measurement outputs of the air sensor; and
   determining whether a standard deviation of the plurality of measurement outputs is smaller than a threshold.

5. The method as claimed in claim 1, further comprising a step of:
   receiving an instruction through a user interface to start or stop any one of the steps i and ii.

6. A non-transitory computer-readable medium embodied with a computer program that comprises a set of instructions executable by a processor for enabling the processor to carry out the method as claimed in claim 1.

7. An air treatment device comprising:

an air purifying unit, configured to purify air;

an air sensor, configured to measure a first air quantity and provide a measurement output, wherein the first air quantity comprises a mixture of ambient air and the air purified by the air purifying unit, and the air treatment device is placed in an airtight space; and a processor, configured to generate a first value based on the measurement output of the air sensor so as to calibrate the air sensor, the processor further being configured to determine whether the quality of the first air quantity in the airtight space meets a predefined criterion, and generate the first value based on the measurement output of the air sensor if the quality of the first air quantity meets the predefined criterion.

8. The air treatment device as claimed in claim 7, further comprising:

a switch arranged between the air sensor and the air purifying unit;

wherein the processor is further configured to open or close the switch to allow the purified air to flow toward the air sensor or to block the purified air to flow toward the air sensor.

9. The air treatment device as claimed in claim 7, further comprising:

a user interface, configured to at least one of (a) receive an instruction and (b) display an operation of the air treatment device.

10. The air treatment device as claimed in claim 7, wherein the air sensor is a particle sensor or a gas sensor.

11. The air treatment device as claimed in claim 7, wherein the processor is further configured to generate a compensation value based on the first value and a reference value so as to calibrate the air sensor, wherein the reference value is a standard output of the air sensor at zero air.

12. The air treatment device as claimed in claim 7, wherein the processor is further configured to:

collect a plurality of measurement outputs of the air sensor; and determine whether a standard deviation of the plurality of measurement outputs is smaller than a threshold.

* * * * *